US006346543B1

(12) United States Patent
Bissery et al.

(10) Patent No.: US 6,346,543 B1
(45) Date of Patent: Feb. 12, 2002

(54) USE OF A TAXOID TO TREAT ABNORMAL CELL PROLIFERATION IN THE BRAIN

(75) Inventors: Marie-Christine Bissery, Vitry sur Seine; Patricia Vrignaud, Combs la Ville, both of (FR); Simon Roberts, Harlow; Clive Brealey, Tring, both of (GB)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/371,838

(22) Filed: Aug. 11, 1999

Related U.S. Application Data
(60) Provisional application No. 60/099,581, filed on Sep. 8, 1998.

(30) Foreign Application Priority Data

Aug. 17, 1998 (EP) .............................................. 98115401

(51) Int. Cl.[7] .......................................... A61K 31/335
(52) U.S. Cl. .................................................... 514/449
(58) Field of Search ........................................ 514/449

(56) References Cited

U.S. PATENT DOCUMENTS 5,847,170 A * 12/1998 Bouchard et al. ........... 549/510

FOREIGN PATENT DOCUMENTS

| EP | 617018 A1 | 9/1994 |
| FR | WO 96/30355 A1 * | 10/1996 |
| FR | 2771092 | 5/1999 |
| WO | WO 94/07878 | 4/1994 |
| WO | WO 96/30335 | 10/1996 |

OTHER PUBLICATIONS

Caubère, P., Unimetal Super Bases, Chem. Rev., vol. 93, pp. 2317–2334 (1993).
Chauvière, G., et al., Chimie Organique Biologique, C.R. Acad. Sc. Paris, vol. 293, Series II, pp. 501–503 (1981).
Schlosser, M., Superbases as Powerful Tools in Organic Syntheses, Mod. Synth. Methods, vol. 6, pp. 227–271 (1992) (Includes English abstract).
Shelanski, M.L., et al., Microtubule Assembly in the Absence of Added Nucleotides, Proc. Nat. Acad. Sci. USA, vol. 70, No. 3, pp. 765–768 (1973).

English language Derwent Abstract of FR 2771092, 1999.
In Vivo Cancer Models, NIH Publication No. 84–2635, pp. 1–33 (1984).
Abstract: Archimbaud, Yves; Gires, P.; Pellerin, R.; Nichele, G.; Poulet, D.; Semiond, D.; Sanderink, G.J., Marietta, M., "Pharmacokinetics of a New Taxoid, 14C–TXD258, in Blood, Plasma and Brain of the Mouse, Rat and Dog," 1st Annual Meeting of the American Association for Cancer Research, Proceedings of the American Association for Cancer Research Annual Meeting, Apr. 1–5, 2000, BIOSIS No. 200000235952.
Abstract: Bissery, Marie–Christine; Bouchard, H.; Riou, J.F.; Vrignaud, P.; Combeau, C.; Bourzat, J.D., Commercon, A.; and Lavelle, F., "Preclinical Evaluation of TXD258, A New Taxoid", 1st Annual Meeting of the American Association for Cancer Research, Proceedings of the American Association for Cancer Research Annual Meeting, Apr. 1–5, 2000, BIOSIS No. 200000239117.

* cited by examiner

Primary Examiner—Dwayne C. Jones
(74) Attorney, Agent, or Firm—Finnegan, Henderson, Farabow, Garrett & Dunner LLP

(57) ABSTRACT

A method for treating abnormal cell proliferation in the brain by administering to a mammal in need thereof an effective amount of a taxoid derivative of formula (I) or a pharmaceutically acceptable salt or solvate thereof, wherein Z represents hydrogen or a radical of formula (II):

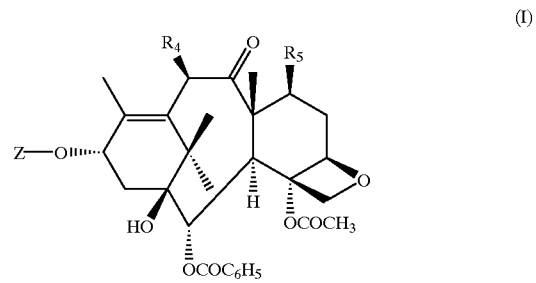

(I)

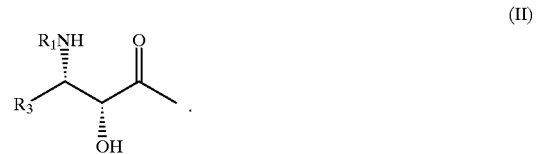

(II)

5 Claims, No Drawings

USE OF A TAXOID TO TREAT ABNORMAL CELL PROLIFERATION IN THE BRAIN

This application claims priority to U.S. Provisional Application No. 60/099,581, filed on Sep. 8, 1998, the entire content of which is incorporated herein by reference.

The present invention provides a new use of taxoid derivatives. More specifically, the present invention provides a method for treating abnormal cell proliferation in the brain of mammals, including humans, by administering a compound of formula (I) or a pharmaceutically acceptable salt or solvate thereof:

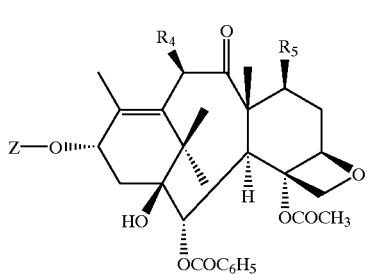

(I)

wherein:

Z represents a hydrogen atom or a radical of formula (II):

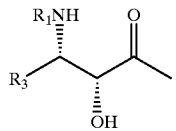

(II)

wherein:
$R^1$ represents:
  a benzoyl radical which is unsubstituted or substituted with at least one identical or different atom or radical selected from halogen atoms and alkyl radicals containing from 1 to 4 carbon atoms, alkoxy radicals containing from 1 to 4 carbon atoms or trifluoromethyl radicals,
  a thenoyl or furoyl radical, or
  a radical $R_2$—O—CO— in which $R_2$ represents:
    an alkyl radical containing from 1 to 8 carbon atoms,
    an alkenyl radical containing from 2 to 8 carbon atoms,
    an alkynyl radical containing from 3 to 8 carbon atoms,
    a cycloalkyl radical containing from 3 to 6 carbon atoms,
    a cycloalkenyl radical containing from 4 to 6 carbon atoms, or
    a bicycloalkyl radical containing from 7 to 10 carbon atoms,
    these radicals being optionally substituted with one or more substituents selected from halogen atoms and hydroxyl radicals, alkoxy radicals containing from 1 to 4 carbon atoms, dialkylamino radicals in which each alkyl portion contains from 1 to 4 carbon atoms, piperidino or morpholino radicals, 1-piperazinyl radicals, which radicals are unsubstituted or substituted at position 4 with an alkyl radical containing from 1 to 4 carbon atoms or with a phenylalkyl radical in which the alkyl portion contains from 1 to 4 carbon atoms, cycloalkyl radicals containing from 3 to 6 carbon atoms, cycloalkenyl radicals containing from 4 to 6 carbon atoms, phenyl radicals which are unsubstituted or substituted with at least one atom or radical selected from halogen atoms and alkyl radicals containing from 1 to 4 carbon atoms or alkoxy radicals containing from 1 to 4 carbon atoms, cyano or carboxyl radicals or alkoxycarbonyl radicals in which the alkyl portion contains from 1 to 4 carbon atoms,
    a phenyl or α- or β-naphthyl radical which is unsubstituted or substituted with at least one atom or radical selected from halogen atoms and alkyl radicals containing from 1 to 4 carbon atoms or alkoxy radicals containing from 1 to 4 carbon atoms,
    a 5-membered aromatic heterocyclic radical preferably selected from furyl and thienyl radicals, or
    a saturated heterocyclic radical containing from 4 to 6 carbon atoms, which is unsubstituted or substituted with at least one alkyl radical containing from 1 to 4 carbon atoms;
$R_3$ represents:
  an unbranched or branched alkyl radical containing from 1 to 8 carbon atoms,
  an unbranched or branched alkenyl radical containing from 2 to 8 carbon atoms,
  an unbranched or branched alkynyl radical containing from 2 to 8 carbon atoms,
  a cycloalkyl radical containing from 3 to 6 carbon atoms,
  a phenyl or α- or β-naphthyl radical which is unsubstituted or substituted with at least one atom or radical selected from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals,
  or a 5-membered aromatic heterocycle containing one or more identical or different hetero atoms selected from nitrogen, oxygen and sulphur atoms, and which is unsubstituted or substituted with at least one identical or different substituent selected from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl and alkoxycarbonyl radicals,
  with the provisos that, in the substituents of the phenyl, α- or β-naphthyl and aromatic heterocyclic radicals, the alkyl radicals and the alkyl portions of the other radicals contain from 1 to 4 carbon atoms, and that the alkenyl and alkynyl radicals contain from 2 to 8 carbon atoms, and that the aryl radicals are phenyl or α- or β-naphthyl radicals;
$R_4$ represents:
  an alkoxy radical containing from 1 to 6 carbon atoms in an unbranched or branched chain,
  an alkenyloxy radical containing from 3 to 6 carbon atoms in an unbranched or branched chain,
  an alkynyloxy radical containing from 3 to 6 carbon atoms in an unbranched or branched chain,
  a cycloalkyloxy radical containing from 3 to 6 carbon atoms, or
  a cycloalkenyloxy radical containing from 4 to 6 carbon atoms, these radicals being which is unsubstituted or substituted with at least one halogen atom or with an alkoxy radical containing from 1 to 4 carbon atoms, an alkylthio radical containing from 1 to 4 carbon atoms or a carboxyl radical, an alkyloxycarbonyl radical in which the alkyl portion contains from 1 to 4 carbon atoms, a cyano or carbamoyl radical or an N-alkylcarbamoyl or N,N-dialkylcarbamoyl radical in which each alkyl portion contains from 1 to 4 carbon atoms or, with the nitrogen atom to which it is linked, forms a saturated 5- or 6-membered heterocyclic radical containing or not containing a second hetero atom selected from oxygen, sulphur, and nitrogen atoms, which is unsubstituted or substituted with an alkyl radical containing from 1 to 4 carbon atoms or a phenyl radical or a phenylalkyl radical in which the alkyl portion contains from 1 to 4 carbon atoms; and $R_5$ represents:

an alkoxy radical containing from 1 to 6 carbon atoms in an unbranched or branched chain, an alkenyloxy radical containing from 3 to 6 carbon atoms, an alkynyloxy radical containing from 3 to 6 carbon atoms, a cycloalkyloxy radical containing from 3 to 6 carbon atoms or a cycloalkenyloxy radical containing from 3 to 6 carbon atoms, these radicals being which is unsubstituted or substituted with at least one halogen atom or with an alkoxy radical containing from 1 to 4 carbon atoms, an alkylthio radical containing from 2 to 4 carbon atoms or a carboxyl radical, an alkyloxycarbonyl radical in which the alkyl portion contains from 1 to 4 carbon atoms, a cyano or carbamoyl radical or an N-alkylcarbamoyl or N,N-dialkylcarbamoyl radical in which each alkyl portion contains from 1 to 4 carbon atoms or, with the nitrogen atom to which it is linked, forms a saturated 5- or 6-membered heterocyclic radical containing or not containing a second hetero atom selected from oxygen, sulphur, and nitrogen atoms, which is unsubstituted or substituted with an alkyl radical containing from 1 to 4 carbon atoms or a phenyl radical or a phenylalkyl radical in which the alkyl portion contains from 1 to 4 carbon atoms.

Both the foregoing general description and the following detailed description of the invention are exemplary and explanatory only and are not necessarily restrictive of the claimed invention.

Preferably, the aryl radicals which can be represented by $R_3$ are phenyl or α- or β-naphthyl radicals which is unsubstituted or substituted with at least one atom or radical selected from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro, and trifluoromethyl radicals, with the provisos that the alkyl radicals and the alkyl portions of the other radicals contain from 1 to 4 carbon atoms, that the alkenyl and alkynyl radicals contain from 2 to 8 carbon atoms, and that the aryl radicals are phenyl or α- or β-naphthyl radicals.

Preferably, the heterocyclic radicals which can be represented by $R_3$ are 5-membered aromatic heterocyclic radicals containing one or more identical or different atoms selected from nitrogen, oxygen, and sulphur atoms, which is unsubstituted or substituted with at least one identical or different substituents selected from halogen atoms (fluorine, chlorine, bromine, iodine) and alkyl radicals containing from 1 to 4 carbon atoms, aryl radicals containing from 6 to 10 carbon atoms, alkoxy radicals containing from 1 to 4 carbon atoms, aryloxy radicals containing from 6 to 10 carbon atoms, amino radicals, alkylamino radicals containing from 1 to 4 carbon atoms, dialkylamino radicals in which each alkyl portion contains from 1 to 4 carbon atoms, acylamino radicals in which the acyl portion contains from 1 to 4 carbon atoms, alkoxycarbonylamino radicals containing from 1 to 4 carbon atoms, acyl radicals containing from 1 to 4 carbon atoms, arylcarbonyl radicals in which the aryl portion contains from 6 to 10 carbon atoms, cyano, carboxyl and carbamoyl radicals, alkylcarbamoyl radicals in which the alkyl portion contains from 1 to 4 carbon atoms, dialkylcarbamoyl radicals in which each alkyl portion contains from 1 to 4 carbon atoms, and alkoxycarbonyl radicals in which the alkoxy portion contains from 1 to 4 carbon atoms.

Preferably, the radicals $R_4$ and $R_5$, which may be identical or different, represent unbranched or branched alkoxy radicals containing from 1 to 6 carbon atoms, which is unsubstituted or substituted with a methoxy, ethoxy, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl, or N-piperidinocarbonyl radical.

More preferably, Z represents a hydrogen atom or a radical of formula (II) in which $R_1$ represents a benzoyl radical or a radical $R_2$—O—CO— in which $R_2$ represents a tert-butyl radical, and $R_3$ represents an alkyl radical containing from 1 to 6 carbon atoms, an alkenyl radical containing from 2 to 6 carbon atoms, a cycloalkyl radical containing from 3 to 6 carbon atoms, a phenyl radical which is unsubstituted or substituted with at least one identical or different atoms or radicals selected from halogen atoms (fluorine, chlorine) and alkyl(methyl), alkoxy(methoxy), dialkylamino(dimethylamino), acylamino(acetylamino), alkoxycarbonylamino(tert-butoxycarbonylamino) and trifluoromethyl radicals, and a 2- or 3-furyl, 2- or 3-thienyl, and a 2-, 4-, or 5-thiazolyl radical, and $R_4$ and $R_5$, which may be identical or different, each represent an unbranched or branched alkoxy radical containing from 1 to 6 carbon atoms.

Still more preferably, Z represents a hydrogen atom or a radical of general formula (II) in which $R_1$ represents a benzoyl radical or a radical $R_2$—O—CO— in which $R_2$ represents a tert-butyl radical, and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl, or 5-thiazolyl radical, and $R_4$ and $R_5$, which may be identical or different, each represent a methoxy, ethoxy, or propoxy radical.

Even more preferably, $R_3$ represents a phenyl radical, $R_1$ represents a tert-butoxycarbonyl radical, and $R_4$ and $R_5$, which may be identical or different, represent a methoxy, ethoxy, or propoxy radical.

Even more preferably, the present invention relates to 4α-acetoxy-2α-benzoyloxy-5β, 20-epoxy-1β-hydroxy-7β, 10β-dimethoxy-9-oxo-11-taxen-13α-yl (2R,3S)-3 tert -butoxycarbonylamino-2-hydroxy-3-phenylpropionate of formula (Ia):

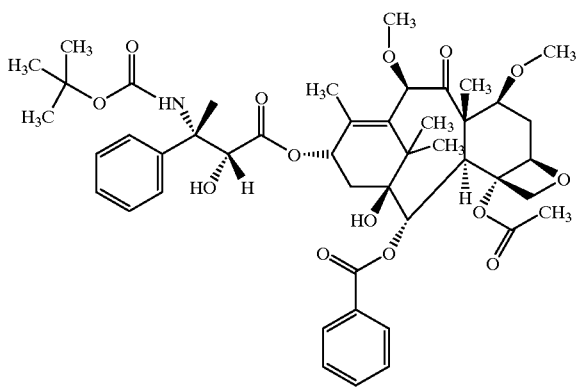

(Ia)

WO 96/30355, the entire content of which is incorporated herein by reference, discloses two processes for preparing a derivative according to the present invention. The first preparatory process is a multi-step process starting with 10-deacetylbaccatin III of formula (III):

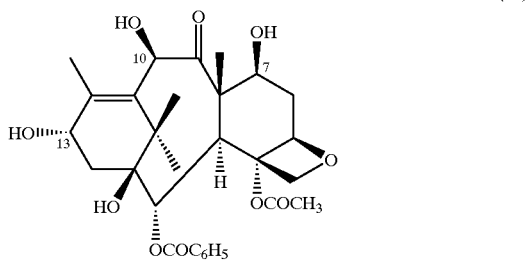

(III)

Compound (III) is selectively protected in positions 7 and 13, for example in the form of a silyl diether, followed by reaction with a product of formula (IV):

R—X   (IV)

in which R represents a radical as defined above, and X represents a reactive ester residue, such as a sulphuric or sulphonic ester residue or a halogen atom, to give a product bearing the unit —OR in position 10 and silyl groups in positions 7 and 13. Next, the silyl protecting groups are replaced with hydrogen atoms to give a compound still bearing the group —OR in position 10, and bearing OH groups in positions 7 and 13. The latter derivative is etherified selectively in position 7 by reaction with the derivative of formula IV to give the derivative of formula (I) in which Z is equal to hydrogen.

The next step involves esterifying in position 13 the derivatives of formula (I), in which Z represents hydrogen, in the presence of a β-lactam, according to a process which is well known to persons of skill in the art, e.g., as described in European patent EP 617,018, or in the presence of an oxazolidine, e.g., as described in patent WO 96/30355. The entire content of EP 617,018 is incorporated herein by reference. After deprotection of the protecting groups in positions 7 and 10, an ester of formula (I) is obtained in which Z is other than hydrogen and R represents hydrogen.

The next step involves reacting the positions 7 and 10 simultaneously by the action of a reagent formed in situ from a sulphoxide of formula (V) and acetic anhydride (Pummerer-type reaction):

R—SO—R   (V)

in which R has the same meaning as defined above, to form a C-7 and C-10 alkylthioalkyloxy intermediate compound.

The final step, which allows the desired compound of formula (I) to be obtained, is carried out on the intermediate compound obtained above by the action of activated Raney nickel.

Generally, the action of the reagent formed in situ from sulphoxide of formula (V), preferably dimethyl sulphoxide and acetic anhydride, is carried out in the presence of acetic acid, or an acetic acid derivative such as a haloacetic acid, at a temperature ranging from 0 to 50° C.

Generally, the action of the activated Raney nickel in the presence of an aliphatic alcohol or an ether is carried out at a temperature ranging from −10 to 60° C.

Another process is described in French patent application FR 97-14442, the entire content of which is incorporated herein by reference. This process allows, in a single step, the direct, selective, and simultaneous alkylation of the two hydroxyl functions in positions 7 and 10 of 10-deacetylbaccatin, or of derivatives thereof esterified in position 13, of formula (VI):

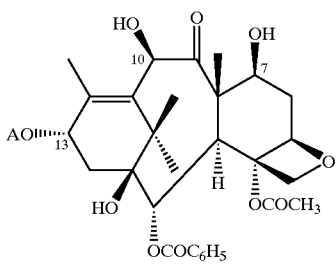

(VI)

in which A represents hydrogen or a side chain of formula (IIa) below:

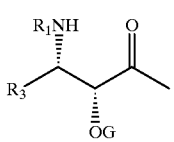

(IIa)

in which G represents a protecting group for the hydroxyl function, and $R_1$ and $R_3$ have the same meaning as in formula (II), or an oxazolidine unit of formula (IIb):

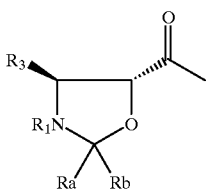

(IIb)

in which $R_1$ and $R_3$ have the same meaning as in formula (II), and $R_a$ and $R_b$, which may be identical or different, represent hydrogen or alkyl, aryl, halo, alkoxy, arylalkyl, alkoxyaryl, haloalkyl, haloaryl, wherein the substituents may optionally form a 4- to 7-membered ring.

It is preferable to use 10-deacetylbaccatin as starting material, i.e., the product of formula (III). This allows appreciable economy in the process and moreover avoids the intermediate protection and deprotection steps necessary in the old processes.

Among the groups G for protecting the hydroxyl function of formula (IIa), it is generally preferred to choose any of the protecting groups described in texts such as Greene and Wuts, *Protective Groups in Organic Synthesis,* 1991, John Wiley & Sons, and MacOmie, *Protective Groups in Organic Chemistry,* 1975, Plenum Press, that are deprotected under conditions that degrade the rest of the molecule little or not at all, e.g.:

ethers, preferably methoxymethyl ether, 1-ethoxyethyl ether, benzyloxymethyl ether, p-methoxybenzyloxymethyl ether, benzyl ethers which is unsubstituted or substituted with at least one groups such as methoxy, chloro, nitro, 1-methyl-1-methoxyethyl ether, 2-(trimethylsilyl)ethoxymethyl ether, tetrahydropyranyl ether, and silyl ethers such as trialkylsilyl ethers; or carbonates such as trichloroethyl carbonates.

The entire content of both cited texts entitled *Protective Groups in Organic Synthesis* is incorporated herein by reference.

Preferably, the radicals $R_a$ and $R_b$ of general formula (IIb) are selected from those described in International patent publication WO 94/07878. More preferably, $R_a$ is hydrogen and $R_b$ is a p-methoxyphenyl radical.

The alkylating agent is selected from:

alkyl halides, preferably alkyl iodides (RI);

alkyl sulphates, such as methyl sulphate; and oxoniums, such as trialkyloxonium boric salts, preferably trimethyloxonium tetrafluoroborate ($Me_3OBF_4$).

Methyl iodide is preferably used.

The alkylating agent is used in the presence of an anionization agent, such as one or more strong bases, in anhydrous medium.

Examples of bases which can be used in anhydrous medium include, but are not limited to:

alkali metal hydrides, such as sodium or potassium hydride;

alkali metal alkoxides, such as potassium tert-butoxide;

silver oxide ($Ag_2O$);

1,8-bis(dimethylamino)naphthalene; and mono- or dimetallic base mixtures such as those described, e.g., in publications such as P. Caubère, Chem. Rev. (1993) 93, 2317–2334 or M. Schlosser, Mod. Synth. Methods (1992) 6, 227–271, the entire content of both publications being incorporated herein by reference; preferably, the alkyllithium/alkali metal t-butoxide or alkali metal amide/alkali metal t-butoxide combinations. One of the two bases can be generated in situ.

The combination of alkylating agent and anionization agent is preferably methyl iodide and potassium hydride.

The reaction is preferably carried out in an organic medium that is inert under the reaction conditions. Among the solvents, it is preferable to use:

ethers such as tetrahydrofuran or dimethoxyethane;

when silver oxide is used, it is preferred to use polar aprotic solvents, e.g., dimethylformamide, or aromatic solvents, e.g., toluene; and when 1,8-bis(dimethylamino)naphthatene is used, it is preferred to use alkylesters such as ethylacetate.

Preferably, the molar ratio between the anionization agent and the substrate is greater than 2, and more preferably ranges from 2 and 20.

Preferably, the molar ratio between the alkylating agent and the substrate is greater than 2, and more preferably ranges from about 2 to about 40.

Preferably, the reaction temperature ranges from about −30° C. to about 80° C.

Preferably, the reaction time ranges from a few hours to about 48 hours, depending on the reagents chosen.

After the alkylating step, when the latter is carried out on 10-deacetylbaccatin, the process then proceeds to the esterification step in a known manner, according, e.g., to the processes described in EP 617,018 or WO 96/30355.

Thus, according to a first 3-step process, the procedure begins with the dialkylation of 10-deacetylbaccatin using an alkylating agent in the presence of a strong base. In a second step, the 10-deacetylbaccatin dietherified in positions 7 and 10 is coupled in position 13 with a suitably protected β-lactam in the presence of an activating agent selected from tertiary amines and metal bases which ensure the formation of an alkoxide in position 13. Deprotection of the side chain is then achieved by the action of an inorganic or organic acid.

According to a second 3-step process, the procedure first begins with the dialkylation of 10-deacetylbaccatin, using an alkylating agent in the presence of a strong base. In a second step, the 10-deacetylbaccatin dietherified in positions 7 and 10 is coupled, in position 13, with an oxazolidine in the presence of a coupling agent such as diimides in the presence of an activating agent such as dialkylaminopyridines. Opening of the oxazolidine is achieved by the action of an inorganic or organic acid.

According to a third process, the procedure begins with the esterification in position 13 of baccatin, suitably protected in positions 7 and 10, with a β-lactam or an oxazolidine in the presence of a coupling agent and/or an activating agent as described in the above two processes. After deprotection in positions 7 and 10, the dietherification in positions 7 and 10 is carried out by an alkylating agent in the presence of a strong base. Deprotection of the side chain is then achieved by the action of an inorganic or organic acid.

The products of general formula (I) have remarkable biological properties.

In vitro, measurement of the biological activity was carried out on tubulin extracted from pig brain by the method of M. L. Shelanski et al., Proc. Natl. Acad. Sci. USA, 70, 765–768 (1973). Study of the depolymerization of the microtubules into tubulin was carried out according to the method of G. Chauvière et al., C. R. Acad. Sci., 293, série II, 501–503 (1981). The entire content of the preceding two articles is incorporated herein by reference.

In vivo, the products of general formula (I) proved active in mice grafted with the B16 melanoma at doses of between 1 and 50 mg/kg intraperitoneally, as well as on other liquid or solid tumors.

The compounds of formula (I) have anti-tumor properties, more particularly, activity against tumors which are resistant to Taxol® and Taxotere®. Such tumors include, for example, brain tumors which have an elevated expression of mdr 1 gene (multi-drug resistant gene).

Multi-drug resistance is the resistance by a tumor against various compounds having differing structures and mechanisms of action. Taxoids are generally known to be highly recognized by experimental tumors such as P388/DOX, a P388 murine leukemia cell line selected for doxorubicin (DOX) resistance, which express mdr 1. The compounds of formula (I) according to the present invention are less recognized by P388/DOX. More particularly, the compounds are less recognized than Taxotere® by mdr 1.

The compounds of formula (I) are mainly used for preparing a medicine for treating abnormal cell proliferation in the brain.

The compound, preferably the compound of formula (I) where $R_4$ and $R_5$ are each methoxy, has the ability to cross the blood brain barrier. It is active compared to the other known taxoids such as Taxol® or Taxotere® for treating brain cancer.

The product of formula (I) can be used concurrently with at least one other therapeutic treatment. It is preferably used with other therapeutic treatments including, but not limited to, antineoplastic drugs, monoclonal antibodies, immunotherapies, radiotherapies, or biological response modifiers. Examples of biological response modifiers include, but are not limited to, lymphokines and cytokines, interleukins, α, β, or δ interfeons, and TNF.

The product of formula (I) is preferably administered by parenteral administration, including, but not limited to, intravenous, intraperitoneal, intramuscular, and subcutaneous administration.

The present invention is further illustrated by the following examples, which are designed to teach those of ordinary skill in the art how to practice the invention. The following examples are illustrative of the invention and should not be construed as limiting the invention as claimed.

EXAMPLES

The product of formula (Ia) has been shown to be a potent anti-cancer agent in pre-clinical models.

Example 1

Analytical Results Obtained from a Single i.v. Bolus Pharmacokinetic Study in Mice.

Groups of female C3H/HeN mice received the product by an intravenous route as a bolus at a dose level of 40 mg.kg$^{-1}$, equivalent to 120 mg.m$^{-2}$. Blood and brain samples were obtained from all dosed animals sacrificed at intervals up to 72 hours post dose. Brain and corresponding plasma samples were assayed for product (Ia) content by an LC-MS/MS assay.

Formulation 2.25 mg.ml$^{-1}$ solution containing 5% Polysorbate 80, 5% ethanol, and 90% of an aqueous 5% glucose solution.

Fifty-six female C3H/HeN mice, each weighing ca 20 g, were each administered formulated product II by i.v. bolus via the tail vein at an injection volume of 0.4 ml to give a total dose of 40 mg.kg$^{-1}$.

Blood and Tissue Sampling

Sampling:
  Blood by cardiac puncture, and liver and brain by dissection after $CO_2$ sacrifice.

Sample Times
  At 2, 5, 15, 30, 45 minutes, and 1, 2, 4, 6, 8, 14, 24, 48 and 72 hours post dose.

Whole blood was collected in heparinised tubes, and corresponding plasma samples were obtained by centrifugation, and frozen immediately at −20° C. Tissues were blotted, weighed, and frozen immediately at −20° C. All samples were dispatched frozen for analysis. Upon receipt, samples were stored frozen at approximately −18° C. pending analysis.

LC-MS/MS Analysis of Brain and Plasma Samples

Detection:
  LC-MS/MS (Sciex API III plus) in turbo-ionspray mode. The following MS conditions were applied:

| | | | |
|---|---|---|---|
| Auxiliary gas flow | 6 L.min$^{-1}$ | | |
| Nebuliser gas flow | 0.6 L.min$^{-1}$ | | |
| Turbo temperature | 450° C. | | |
| CGT | 300 | Curtain gas | |
| flow | 0.6 L.min$^{-1}$ | Scan time | 1 |
| scan/sec | | Eluent split ratio | 1:10 |

Column:
  75×4.6 mm Supelcosil ABZ plus (3 μm).
Mobile phase:
  Acetonitrile/methanol/ammonium acetate (10 mM); 40/25/35 v/v/v.
Flow rate:
  1 ml.min$^{-1}$.
Temperature:
  Ambient.
Extraction
  Plasma: Added 100 μl of acetonitrile to sample (50 μl). Vortexed, centrifuged, removed supernatant, added 100 μl of mobile phase and injected 150 μl.
  Brain: Added 100 μl of acetonitrile to homogenised sample (100 mg of a 1:1 w/w brain with water homogenate) and vortexed. Added 1 ml of diethyl ether, vortexed, centrifuged, removed organic layer, and dried under $N_2$. Reconstituted in 200 μl of mobile phase and injected 150 μl.
Calibration standards:
  Plasma: Nine at concentrations of 5, 10, 20, 50, 100, 200, 300, 400 & 500 ng.ml$^{-1}$ (product Ia). Prepared by adding suitable aliquots of the product (concentrations =0.1, 1 or 10 μg.ml$^{-1}$) in ethanol to 0.5 ml aliquots of mouse plasma. Each sample was vortexed following drug addition; a 50 µl aliquot was then removed for assay.

Brain: Eleven at concentrations of 10, 20, 30, 100, 200, 300, 400, 500, 1000, 2500 & 5000 ng.g$^{-1}$ in homogenised mouse brain (1:1 w/w brain with water). Prepared by adding suitable aliquots of the product (concentrations=1, 10 or 100 µg.ml-$^{-1}$) in ethanol to 0.5, 1, 3 or 4 g of homogenised mouse brain. Each sample was vortexed following drug addition and a 100 mg aliquot was then removed for assay.

Retention times:

Drug; product (Ia): ~2.3 min.

Extraction efficiency:

Plasma: ca. 58 % at 200 ng.ml-$^{-1}$.

Brain: ca. 41 % at 500 ng.g$^{-1}$ and 39 % at 1000 ng.g$^{-1}$.

Results

Plasma Levels

The following table contains product (Ia) plasma levels observed after i.v. administration of product (Ic) at a dose level of 40 mg.kg$^{-1}$ to the mouse.

TABLE 1

Preliminary plasma concentrations of product (Ia) after i.v. dosing at a level of 40 mg.kg$^{-1}$ to the mouse.

| Time after dose | Plasma product (Ic) concentration (ng.ml$^{-1}$) | | | | | |
|---|---|---|---|---|---|---|
| | IV1 | IV2 | IV3 | IV4 | MEAN | ±s.d. |
| 2 min | 52987 | 45942 | 49607 | 38994 | 46882 | 5994 |
| 5 min | 36734 | 33538 | 32077 | 34903 | 34313 | 1984 |
| 15 min | 20493 | 20897 | 21051 | 19459 | 20475 | 717 |
| 0.5 h | 10765 | 10344 | 9170 | 11232 | 10378 | 883 |
| 0.75 h | 7133 | 10948 | 8121 | 10148 | 9087 | 1764 |
| 1 h | 6017 | 7423 | 6693 | 6079 | 6553 | 655 |
| — | 4633 | 4337 | 4600 | 3564 | 4283 | 498 |
| 4 h | 1072 | 1110 | 835 | 830 | 962 | 150 |
| 6 h | 449 | 316 | 346 | 336 | 362 | 59 |
| 8 h | 204 | 199 | 195 | 154 | 188 | 23 |
| 14 h | 65 | 56 | 50 | 52 | 56 | 7 |
| 24 h | 18(blq) | 15(blq) | 15(blq) | 16(blq) | 16 | 1 |
| 48 h | 4(blq) | n.d. | n.d. | 4(blq) | 2 | 2 |
| 72 h | n.d. | n.d | n.d | n.d. | — | n.a. | n.a.: not applicable
n.d.: not detected (≤l.o.d. of 4 ng.ml$^{-1}$)
blq: below limit of accurate quantification (20 ng.ml$^{-1}$).

Brain Levels

The following table contains product (Ia) whole brain levels observed after i.v. administration of product (Ia) at a dose level of 40 mg.kg$^{-1}$ to the mouse.

TABLE 2

Preliminary brain concentration for product (Ic) after i.v. dosing at a level of 40 mg.kg$^{-1}$ to the mouse.

| Time after dose | Plasma product (Ic) concentration (ng.ml$^{-1}$) | | | | | |
|---|---|---|---|---|---|---|
| | IV1 | IV2 | IV3 | IV4 | MEAN | ±s.d. |
| 2 min | 6962 | 8817 | 8147 | 7630 | 7889 | 786 |
| 5 min | 8344 | 8473 | 7762 | 8091 | 8167 | 313 |
| 15 min | 5809 | 7100 | 7641 | 6481 | 6758 | 791 |
| 0.5 h | 7262 | 6788 | 8317 | 6894 | 7315 | 698 |
| 0.75 h | 7675 | 8086 | 7513 | 7272 | 7637 | 342 |
| 1 h | 6424 | 8964 | 1747 | 7489 | 6156 | 3118 |
| 2 h | 7956 | 8418 | 6966 | 7017 | 7589 | 716 |
| 4 h | 7909 | 6939 | 6712 | 5459 | 6755 | 1008 |
| 6 h | 6688 | 7968 | 7350 | 3712 | 6430 | 1886 |

TABLE 2-continued

Preliminary brain concentration for product (Ic) after i.v. dosing at a level of 40 mg.kg$^{-1}$ to the mouse.

| Time after dose | Plasma product (Ic) concentration (ng.ml$^{-1}$) | | | | | |
|---|---|---|---|---|---|---|
| | IV1 | IV2 | IV3 | IV4 | MEAN | ±s.d. |
| 8 h | 9067 | 6977 | 8616 | 8342 | 8250 | 900 |
| 14 h | 9618 | 10049 | 7595 | 9271 | 9133 | 1074 |
| 24 h | 7905 | 9842 | 7885 | 9052 | 8671 | 952 |
| 48 h | 6660 | 8541 | 7704 | 7986 | 7723 | 789 |
| 72 h | 5899 | 5511 | 5692 | 3894 | 5249 | 917 | n.d.: not detected (<l.o.d. of 92 ng.g$^{-1}$)
n.a.: not applicable

Pharmacokinetic Parameters

The following table contains the preliminary pharmacokinetic parameters for product (Ic) derived after i.v. administration to the mouse at 40 mg.kg$^{-1}$, calculated using mean plasma and brain level data.

TABLE 3

Preliminary mean pharmacokinetic data.

| Sample | AUC0-∞ (h.µg.ml$^{-1}$ or .g$^{-1}$) | ClT (l.h$^{-1}$.kg$^{-1}$) | Vdss (l.kg$^{-1}$) | Initial T½ (h) | Terminal T½ (h) |
|---|---|---|---|---|---|
| Plasma+ | 30.0 | 1.3 | 1.9 | 0.7 | 6.2 |
| Plasma# | 29.8 | 1.3 | 2.4 | 0.2 | 2.0 |
| Brain | 787.g* | n.a. | n.a. | — | 31.4 |

+calculated from values ≥l.o.d. of 4 ng.ml$^{-1}$
calculated from values ≥b.l.q. of 20 ng.ml$^{-1}$
*the corresponding AUC$_{0-72h}$ = 549.7 h.µg.g$^{-1}$ Key:

AUC$_{0-\infty}$:

Area under the plasma or brain concentration versus time curve from t=0 (start of infusion) to infinity.

Initial T$_{1/2}$:

Initial (distribution) half-life.

Terminal T$_{1/2}$:

Terminal (elimination) half-life (should be regarded as an estimate only being dependent on sampling frequency in the terminal phase and assay sensitivity).

ClT:

Total plasma clearance.

Vdss:

Volume of distribution at steady state.

n.a.:

Not applicable.

A biexponential equation was fitted to the profiles using an interactive linear least-square algorithm as part of the SIPHAR package. AUC was calculated by the trapezoidal rule from time 0 to both the time of the last value that was equal to or greater than the .o.d.+(4 ng.ml$^{-1}$) or the .o.q.#(20 ng.ml$^{-1}$) for plasma and up to 72 h post dose for the brain, and then extrapolated to infinity.

CONCLUSIONS

Product (Ic) levels were high, as would be expected after an i.v. dose of 40 mg.kg$^{-1}$, but declined rapidly from the peak at 2 minutes (mean of 46.9 µg.ml$^{-1}$) to less than 1 µg.ml$^{-1}$ within 4 h (initial half-life of ≤0.7 h). However, levels persisted above the limit of accurate quantification (20 ng.ml$^{-1}$) up to 14 h post dose and consistently above the limit of detection (4 ng.ml$^{-1}$) for up to 24 h post dose.

A terminal half-life of 6.2 h was calculated from detectable plasma levels ($\geqq$24 ng.ml$^{-1}$). However, the terminal half-life is very dependent on assay sensitivity in this case, and if levels above the limit of accurate quantification (20 ng.ml$^{-1}$) are utilized to calculate pharmacokinetic parameters instead, then the terminal half-life drops to 2.0 h.

Mean total plasma clearance was determined to be 1.3 l.h$^{-1}$.kg$^{-1}$, which represented a significant fraction of average liver plasma flow (based on average liver blood flow of ca 5.2 l.h$^{-1}$.kg$^{-1}$).

In this species post-i.v. administration, product (Ic) appeared to readily penetrate the blood brain barrier. High levels were detected at the first sampling time (7.9 $\mu$g.g$^1$ at 2 mins), indicating rapid uptake into this tissue. Although peak levels of 9.1 $\mu$g.g$^{-1}$ were observed at 14 h, high concentrations were sustained up to the last sampling time (5.3 $\mu$g.g$^{-1}$ at 72 h). Not surprisingly, the product was slowly cleared from the brain, with a half-life of 31.4 h. On the basis of AUC$_{0\infty}$ values (788 h.$\mu$g.g$^{-1}$ versus 30 h.$\mu$g.ml$^{-1}$), product Ia levels in the brain were about twenty times those in the plasma.

Example 2

Evaluation of Product (Ia) for Antitumor Activity Against Intracranially Implanted Human Glioblastomas U251 and SF-295 in NCr-nu Mice Four studies were initiated to evaluate the response of U251 and SF-295 glioblastomas to treatment with product (Ia). In the two studies, U251 and SF-295 glioblastomas were initiated from intracranially implanted cells at a volume of 10$^6$ cells per mouse. The treatment schedule of the intracranially implanted U251 glioblastoma cells was iv, once daily, every sixth day for three treatments (q6d×3), beginning on day four post-implant. The treatment schedule of the intracranially implanted SF-295 glioblastoma cells was iv, once daily, every fourth day for three treatments (q4d×3), beginning on day two post-implant. For the intracranially implanted studies, the compounds were evaluated based on their ability to increase the life span of the animals. The positive control used for both of these tumor models was nitrosourea.

The objective of this experiment was to evaluate the product (Ia) for antitumor effect against human glioblastoma tumor models.

In these experiments, general DCTD, NCI techniques and procedures for in vivo efficacy studies were modified for special application (In Vivo Cancer Models, NIH Publication No. 84-2635, 1984). These studies were conducted in approved facilities (AAALAC Registration No. 000643, AALAS Membership No. 840723001, USDA Registration No. 64-R-001, OPPR, PHS, NIH, AWA, Assurance No. A3046-01). These facilities are ISO 9001 certified. The oversight committee was the Southern Research Institutional Animal Care and Use Committee; the protocol used was IACUC No. 96-8-50.

Dilutions:
  Product (Ia) was prepared in 5% ethanol, 5% tween 80, 90% D5W

Nitrosourea was prepared in 2% ethanol, 98% physiological saline.

Dose Preparation:
  All dosing solutions were prepared at Southern Research Institute.

Compound Administration:
  Product (Ia) was administered in 0.4 ml/mouse based on a total body weight average.
  Nitrosourea was administered 0.1 ml/10 g of body weight.

Compound Stability:
  Product (Ia) was kept on ice and administered within 20 minutes of preparation.
  Nitrosourea was kept on ice and administered within 45 minutes of preparation.

Storage Conditions:
  All compounds were stored in refrigerated desiccators.

Handling Precautions:
  The compounds were handled according to procedures required by the Safety Committee of Southern Research Institute. All technicians were fully gowned and gloved with face mask and safety glasses during compound administration.
  Any intracranially implanted animal that appeared to be moribund was euthanized for humane purposes. Since efficacy studies fall within this category of basic research, experiment termination was based on resultants that were determined to be optimal.

Species:
  Six to eight week old athymic NCr-nu female mice were used for the intracranially implanted U251 trials. Six to eight week old athymic NCr-nu male mice were used for the intracranially implanted SF-295 trials.

Justification:
  Immune deficient mice are necessary for the propagation of human tumor xenografts, which was the target tissue for the compounds being developed.

Source:
  FCRDC (Animal Production Area), Frederick, Md., for intracranially implanted SF-295 trial; Taconic Animal Farms, Germantown, NY, for intracranially implanted U251 trials.

Number and Sex:
  A total of 160 males were used on the intracranially implanted SF-295 trials a total of 154 females were used on the intracranially implanted U251 trials.

Weight and age:
  Mean weights were taken at the time each trial was initiated. The mean weight of the mice implanted intracranially with U251 glioblastoma was 21 to 22 g. The mean weight of the mice implanted intracranially with SF-295 glioblastoma was 24 to 26 g.

Animal Identification:
  Standard ear marks.

Quarantine:
  All animals were held for a seven-day observation period before being put into the test.

Housing and Sanitation:
  The animals were housed in filter-capped isolator cages, five per cage. The cages and bedding were changed twice weekly.

Food and Water:
  Teklad Sterlizable 8656 Mouse Diet (Harlan Teklad) was given ad libitum. Filtered tap water was provided ad libitum.

Environmental Conditions:
Maintained according to SRI standard operating procedures approved by the IACUC committee.

Two experiments were involved in this study (RP-36 and RP-38).

As previously mentioned, this experiment was designed to evaluate the activity of product (Ia) against intracranially U251 and SF-295 glioblastomas in athymic MCr-nu mice. The dosages for product (Ia) were 30, 20 and 13.4 mg/kg/dose. For the two intracranially implanted experiments, cells were prepared at a concentration of $3.33 \times 10^7$ cells per ml of media and injected at a volume of 0.03 ml per mouse. The cells were injected into the cerebrum to the right of the midline with a 25 gauge, ⅜ inch, stainless steel needle. Cultured cells were used for the U251 experiment (RP-36). The treatment schedule was q6d×3, iv, beginning on day four, post-implant. A tumor brei, made from solid tumor, was used for the SF-295 experiment (RP-38). The treatment schedule was q4d×3, iv, beginning on day two, post-implant. Nitrosourea was given in each experiment for comparative purposes because of its known activity against CNS tumors. The dosages were 27, 18 and 12 mg/kg/dose and the treatment schedule was the same as the treatment schedule for product (Ia) in each experiment.

In the first experiment (RP-36), each compound was effective in the treatment of intracranially implanted U251 glioblastoma. Treatment with product (Ia) resulted in five of ten, four of ten and three of ten 122-day survivors and an ILS of 176%, 202% and 144% respectively, for the dosage groups, of 30, 20 (MTD) and 13.4 mg/kg/dose. Treatment with nitrosourea resulted in an ILS of 205% and 51% in the dosage groups of 18 and 12 mg/kg/dose, respectively. There were ten of ten and seven of ten 122-day survivors in the dosage groups of 27 (MTD) and 18 mg/kg/dose.

In the second experiment (RP-38), each compound was effective in the treatment of intracranially implanted SF-295 glioblastoma. Treatment with product (Ia) at 30, 20 and 13.4 (MTD) mg/kg dose resulted in an ILS of −9%, 94% and 81%, respectively. There was some toxicity at the dosage levels of 30 and 20 mg/kg dose as evidenced by a respective 7 g and 6 g mean weight loss through the treatment period. There was one 68-day survivor out of ten animals in the dosage group of 13.4 mg/kg/dose. Nitrosourea was toxic at the highest dosage level of 27 mg/kg dose as evidenced by a 7 g mean weight loss through the treatment period. Treatment with nitrosourea at dosages of 27, 18 and 12 mg/kg/dose resulted in an ILS of 50%, 131% and 106%, respectively. There were two 68-day survivors out of ten animals at the dosage level of 27 (MTD) mg/kg/dose, and there was one 68-day survivor out of ten animals at the dosage level of 18 mg/kg/dose.

In summary product (Ia) was tested against both intracranially implanted U251 and SF-295 glioblastomas. This compound was quite active against these two tumor lines at both implant sites.

| | | | | | | | | | | | | | | | |
|---|---|---|---|---|---|---|---|---|---|---|---|---|---|---|---|
| RESPONSE OF IC IMPLANTED U251 GLIOBLASTOMA TO TREATMENT WITH PRODUCT (Ia) ||||||||||||||||
| TREATMENT: IV, Q6D × 3(4) |||||||||||| 122-DAY | MEDIAN | | |
| GROUP # | AGENT | DOSAGE (MG/KG/DOSE) | DAYS OF DEATH |||||||||| SURV./ TOTAL | DAY OF DEATH | % ILS |
| 1 | CONTROL (TREATED) | | 26 34 | 31 37 | 31 37 | 34 39 | 34 41 | 34 43 | 34 45 | 34 80 | 34 115 | 34 — | 1/20 | 34.0 | |
| 8 | Product I(a) | 30.0 | 21 S | 34 | 94 | 98 | 103 | — | — | — | — | — | 5/10 | 94.0 | +176 |
| 9 | | 20.0 | 58 | 98 | 100 | 106 | 106 | 122 | — | — | — | — | 4/10 | 103.0 | +202 |
| 10 | | 13.4 | 69 S | 69 S | 83 | 83 | 83 | 83 | 122 | — | — | — | 3/10 | 83.0 | +144 |
| 14 | Nitrosourea | 27.0 | — | — | — | — | — | — | — | — | — | — | 10/10 | — | — |
| 15 | | 18.0 | 94 | 104 | 104 | — | — | — | — | — | — | — | 7/10 | 104.0 | +205 |
| 16 | | 12.0 | 41 | 45 | 49 | 49 | 49 | 54 | 66 | 69 S | 69 | 80 | 0/10 | 51.5 | +51 |

U251 GLIOBLASTOMA;
TUMOR SOURCE: CELL CULTURE;
IMPLANTED: 04/17/98;
EVALUATION DATE: 08/17/98;
ATHYMIC NCr-nu MICE - FEMALE - TACONIC FARMS
CONTROL, 2% EtOH/SALINE;
INJECTION VOLUME = 0.1 cc/10 g BODY WEIGHT.
Product I(a), BATCH BFC611, PREPARED FROM LOT NO. 1 IN 5% EtOH/5% TWEEN 80/90% D5W (SOLUBLE); INJECTION VOLUME = 0.4 cc.
Nitrosourea PREPARED FROM LOT NO. 2 IN 2% EtOH/SALINE (SOLUBLE);
INJECTION VOLUME = 0.1 cc/10 g BODY WEIGHT.
NOTE:
1) 122-DAY SURVIVORS NOT USED IN CALCULATIONS. MEDIANS CALCULATED BY USING ALL DEATHS.
2) S = SACRIFICED, ANIMAL MORIBUND (USED IN CALCULATIONS).

| RESPONSE OF IC IMPLANTED SF-295 GLIOBLASTOMA TO TREATMENT WITH PRODUCT (Ia) ||||||||||||||||
|---|---|---|---|---|---|---|---|---|---|---|---|---|---|---|---|
| TREATMENT: IV, Q4D × 3(2) ||||||||||||||||
| GROUP # | AGENT | DOSAGE (MG/KG/DOSE) | MEAN ANIMAL WEIGHT IN GRAMS ON DAYS INDICATED |||||||||||||
| | | | 2 | 5 | 8 | 13 | 15 | 19 | 22 | 26 | 29 | 33 | 37 | 40 | 43 |
| 1 | CONTROL (TREATED) | | 25 | 27 | 27 | 21 | 20 | 17 | | | | | | | |
| 8 | Product (Ia) | 30.0 | 25 | 23 | 18 | 18 | 19 | 19 | 21 | 21 | 19 | 20 | 18 | 21 | 17 |
| 9 | | 20.0 | 25 | 24 | 21 | 19 | 18 | 19 | 21 | 22 | 19 | 23 | 29 | 29 | 29 |
| 10 | | 13.4 | 25 | 24 | 23 | 22 | 20 | 21 | 22 | 21 | 22 | 22 | 26 | 22 | 27 |
| 14 | Nitrosourea | 27.0 | 24 | 23 | 21 | 17 | 17 | 16 | 18 | 15 | 19 | 19 | 23 | 24 | 25 |
| 15 | | 18.0 | 26 | 26 | 26 | 25 | 26 | 25 | 28 | 26 | 26 | 24 | 29 | 30 | 33 |
| 16 | | 12.0 | 25 | 24 | 24 | 23 | 25 | 24 | 23 | 25 | 20 | 18 | 14 | | |

| TREATMENT: IV, Q4D × 3(2) |||||||||||||| 68 DAY | MEDIAN | |
|---|---|---|---|---|---|---|---|---|---|---|---|---|---|---|---|
| GROUP # | AGENT | DOSAGE (MG/KG/DOSE) | DAYS OF DEATH |||||||||| SURV./ TOTAL | DAY OF DEATH | % ILS |
| 1 | CONTROL (TREATED) | | 10 | 13 | 14 | 14 | 14 | 14 | 15 | 15 | 16 | 16 | 0/20 | 16.0 | |
| | | | 16 | 17 | 17 | 18 | 18 | 18 | 19 | 20 | 20 | 20 | | | |
| 8 | Product (Ia) | 30.0 | 11 | 13 | 13 | 14 | 14 | 15 | 30 | 40 | 41 | 47 | 0/10 | 14.5 | −9 |
| 9 | | 20.0 | 13 | 13 | 16 | 31 | 31 | 31 | 33 | 33 | 37 | 54 | 0/10 | 31.0 | +94 |
| 10 | | 13.4 | 25 | 25 | 29 | 29 | 29 | 30 | 32 | 34 | 41 | — | 1/10 | 29.0 | +81 |
| 14 | Nitrosourea | 27.0 | 15 | 16 | 16 | 19 | 29 | 37 | 56 | 64 S | — | — | 2/10 | 24.0 | +50 |
| 15 | | 18.0 | 33 | 34 | 34 | 35 | 37 | 37 | 37 | 40 | 41 | — | 1/10 | 37.0 | +131 |
| 16 | | 12.0 | 22 | 23 | 26 | 26 | 33 | 33 | 33 | 33 | 33 | 40 | 0/10 | 33.0 | +106 |

SF-295 GLIOBLASTOMA;
TUMOR SOURCE: 01/A/05F3T8;
IMPLANTED: 08/26/98;
ATHYMIC NCr-nu MICE - MALE - FREDERICK CANCER RESEARCH DEVELOPMENT CENTER
CONTROL, 2% EtOH/SALINE;
INJECTION VOLUME = 0.1 cc/10 g BODY WEIGHT.
Product I(a), BATCH BFC6I1, PREPARED FROM SRI LOT NO. 1 IN 5% EtOH/5% TWEEN 80/90% D5W (SOLUBLE);
INJECTION VOLUME = 0.4 cc.
Nitrosourca BRISTOL-MYERS LOT LAH84, PREPARED FROM SRI LOT NOS. 2–4 IN 2% EtOH/SALINE (SOLUBLE);
INJECTION VOLUME = 0.1 cc/10 g BODY WEIGHT.
NOTE:
1) 68-DAY SURVIVORS NOT USED IN CALCULATIONS, MEDIANS CALCULATED BY USING ALL DEATHS.
2) S = SACRIFICED DUE TO PARALYSIS (USED IN CALCULATIONS).

This application is based on European Application No. EP 98 115 401.6, filed Aug. 17, 1998, the entire content of which is incorporated herein by reference.

The foregoing written description relates to various embodiments of the present invention. Numerous changes and modifications may be made therein without departing from the spirit and scope of the invention as defined in the following claims.

We claim:

1. A method for treating abnormal cell proliferation in the brain, comprising administering to a mammal in need thereof an effective amount of 4α-acetoxy-2α-benzoyloxy, 5β,20-epoxy-1β-hydroxy-7β,10β-dimethoxy-9-oxo-11-taxen-13α-yl(2R,3S)-3-tert-butoxycarbonylamino-2-hydroxy-3-phenyl-propionate, or a pharmaceutically acceptable salt or solvate thereof, wherein said compound or salt or solvate thereof crosses the blood-brain barrier.

2. A method according to claim 1, wherein the abnormal cell proliferation is cancer.

3. A method according to claim 1, wherein the method is performed concurrently with at least one additional therapeutic treatment.

4. A method according to claim 3, wherein the additional therapeutic treatment comprises administering an effective amount of at least one antineoplastic drug, monoclonal antibody, immunotherapy, radiotherapy, or biological response modifier.

5. A method according to claim 4, wherein the additional therapeutic treatment comprises administering at least one response modifier comprising lymphokine, cytokine, interleukin, α, β, or δ interferon, or TNF.

* * * * *